US008403902B2

(12) United States Patent
Locke et al.

(10) Patent No.: US 8,403,902 B2
(45) Date of Patent: Mar. 26, 2013

(54) REDUCED-PRESSURE MEDICAL SYSTEMS AND METHODS EMPLOYING A MOISTURE PROCESSING DEVICE

(75) Inventors: Christopher Brian Locke, Bournemouth (GB); Timothy Mark Robinson, Basingstoke (GB); Aidan Marcus Tout, Alderbury (GB)

(73) Assignee: KCI Licensing, Inc., San Antonio, TX (US)

( * ) Notice: Subject to any disclaimer, the term of this patent is extended or adjusted under 35 U.S.C. 154(b) by 24 days.

(21) Appl. No.: 13/108,753

(22) Filed: May 16, 2011

(65) Prior Publication Data

US 2011/0288512 A1 Nov. 24, 2011

Related U.S. Application Data

(60) Provisional application No. 61/417,670, filed on Nov. 29, 2010, provisional application No. 61/359,205, filed on Jun. 28, 2010, provisional application No. 61/345,821, filed on May 18, 2010.

(51) Int. Cl.
*A61M 1/00* (2006.01)
(52) U.S. Cl. ............ 604/319; 604/538; 433/91; 137/205
(58) Field of Classification Search .................... 604/319
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |

(Continued)

FOREIGN PATENT DOCUMENTS

AU 550575 A1 8/1982
AU 745271 4/1999

(Continued)

OTHER PUBLICATIONS

N. A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96.

(Continued)

*Primary Examiner* — Leslie Deak
*Assistant Examiner* — Jordan B Bailey

(57) ABSTRACT

Systems, methods, and devices related to removing fluids from a patient are provided. In one instance, fluid is removed from the patient and delivered to a canister using reduced pressure. Reduced pressure is supplied to the canister via a reduced-pressure delivery conduit that includes a moisture processing device and a hydrophobic filter. The moisture processing device condenses moisture from the air to prevent condensation from occluding the hydrophobic filter. The moisture processing devices includes an expanded volume and one or more liquid-impermeable, vapor-permeable membranes. The liquid-impermeable, vapor-permeable membrane allows vapor to egress the moisture processing device. Other systems, methods, and devices are presented.

19 Claims, 5 Drawing Sheets

U.S. PATENT DOCUMENTS

| | | |
|---|---|---|
| 4,165,748 A | 8/1979 | Johnson |
| 4,184,510 A | 1/1980 | Murry et al. |
| 4,228,798 A | 10/1980 | Deaton |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,004,915 B2 * | 2/2006 | Boynton et al. ............ 601/6 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0252377 A1 * | 11/2005 | Coan et al. ............ 96/4 |
| 2007/0219532 A1 * | 9/2007 | Karpowicz et al. ........ 604/540 |
| 2009/0221990 A1 | 9/2009 | Jaeb et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 03/018098 A2 | 3/2003 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: "New and Established Methods, *Chronic Wound Care*, edited by D. Krasner (Health Management Publications, Inc., King of Prussia, PA 1990), pp. 240-246.

G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164.
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax, "*Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gork , U.S.S.R. 1987) ("Solovev Guidelines").
V.A. Kuznetsov & N. A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).
International Search Report and Written Opinion date mailed Sep. 29, 2011 for PCT International Application No. PCT/US2011/036875.

\* cited by examiner

REDUCED-PRESSURE MEDICAL SYSTEMS AND METHODS EMPLOYING A MOISTURE PROCESSING DEVICE

RELATED APPLICATIONS

The present invention claims the benefit, under 35 USC §119(e), of the filing of U.S. Provisional Patent Application Ser. No. 61/417,670, entitled "Reduced-Pressure Medical Systems and Methods Employing A Moisture Processing Device," filed 29 Nov. 2010, which is incorporated herein by reference for all purposes; U.S. Provisional Patent Application Ser. No. 61/359,205, entitled "Evaporative Body Fluid Containers and Methods," filed 28 Jun. 2010, which is incorporated herein by reference for all purposes; and U.S. Provisional Patent Application Ser. No. 61/345,821, entitled "Reduced-Pressure Treatment Systems and Methods Employing A Fluidly Isolated Pump Control Unit," filed 18 May 2010, which is incorporated herein by reference for all purposes.

BACKGROUND

The present disclosure relates generally to reduced-pressure medical treatment systems and, more particularly, but not by way of limitation, to reduced-pressure systems, devices, and methods employing a moisture processing device.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue. In more general applications, reduced pressure may be used to remove other fluids from a patient.

SUMMARY

Improvements to existing medical devices, systems, and methods may be realized by the devices, systems, and methods of the illustrative, non-limiting embodiments described herein. According to an illustrative, non-limiting embodiment, a system for removing fluids from a patient using reduced pressure includes a liquid receptor for receiving fluids from the patient, a canister fluidly coupled to the liquid receptor for receiving the fluids from the patient, a reduced-pressure delivery conduit, a reduced-pressure source fluidly coupled by the reduced-pressure delivery conduit to the canister, and a moisture processing device fluidly coupled to the reduced-pressure delivery conduit. The moisture processing device includes a housing having an inlet and an outlet and forming an expanded volume to condense water from air entering the inlet and includes a first liquid-impermeable, vapor-permeable membrane forming at least a portion of the housing. The first liquid-impermeable, vapor-permeable membrane allows vapor in the expanded volume to egress the expanded volume. The system may also include a first hydrophobic filter fluidly coupled to the reduced-pressure delivery conduit.

According to another illustrative, non-limiting embodiment, a method for removing fluids from a patient using reduced pressure includes removing fluids from the patient with reduced pressure, delivering the fluids to a canister, and delivering reduced pressure to the canister through a reduced-pressure delivery conduit from a reduced-pressure source, whereby a fluid flow is created in the reduced-pressure delivery conduit. The method further includes removing moisture from the fluid flow. The step of removing moisture includes receiving the fluid flow, lowering the temperature of the fluid flow in a moisture processing device to condense water from the fluid flow to produce a drier fluid flow, and exposing the condensed water to a liquid-impermeable, vapor-permeable membrane to allow evaporated water to egress the moisture processing device. The method may also include exposing the drier fluid flow to a first hydrophobic filter.

According to another illustrative, non-limiting embodiment, a method of manufacturing a system for removing fluids from a patient with reduced pressure includes forming a liquid receptor, fluidly coupling a canister to the fluid receptor for receiving the fluids from the patient, providing a reduced-pressure delivery conduit, fluidly coupling a reduced pressure source via the reduced-pressure delivery conduit to the canister, and fluidly coupling a moisture processing device to the reduced-pressure delivery conduit. The moisture processing device includes a housing having an inlet, an outlet, and an expanded volume to condense water from air entering the inlet. The moisture processing device further includes a first liquid-impermeable, vapor-permeable membrane that forms at least a portion of the housing. The first liquid-impermeable, vapor-permeable membrane allows vapor in the expanded volume to egress the expanded volume. The method may further comprise fluidly coupling a first hydrophobic filter to the reduced-pressure delivery conduit.

Other features and advantages of the illustrative, non-limiting embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
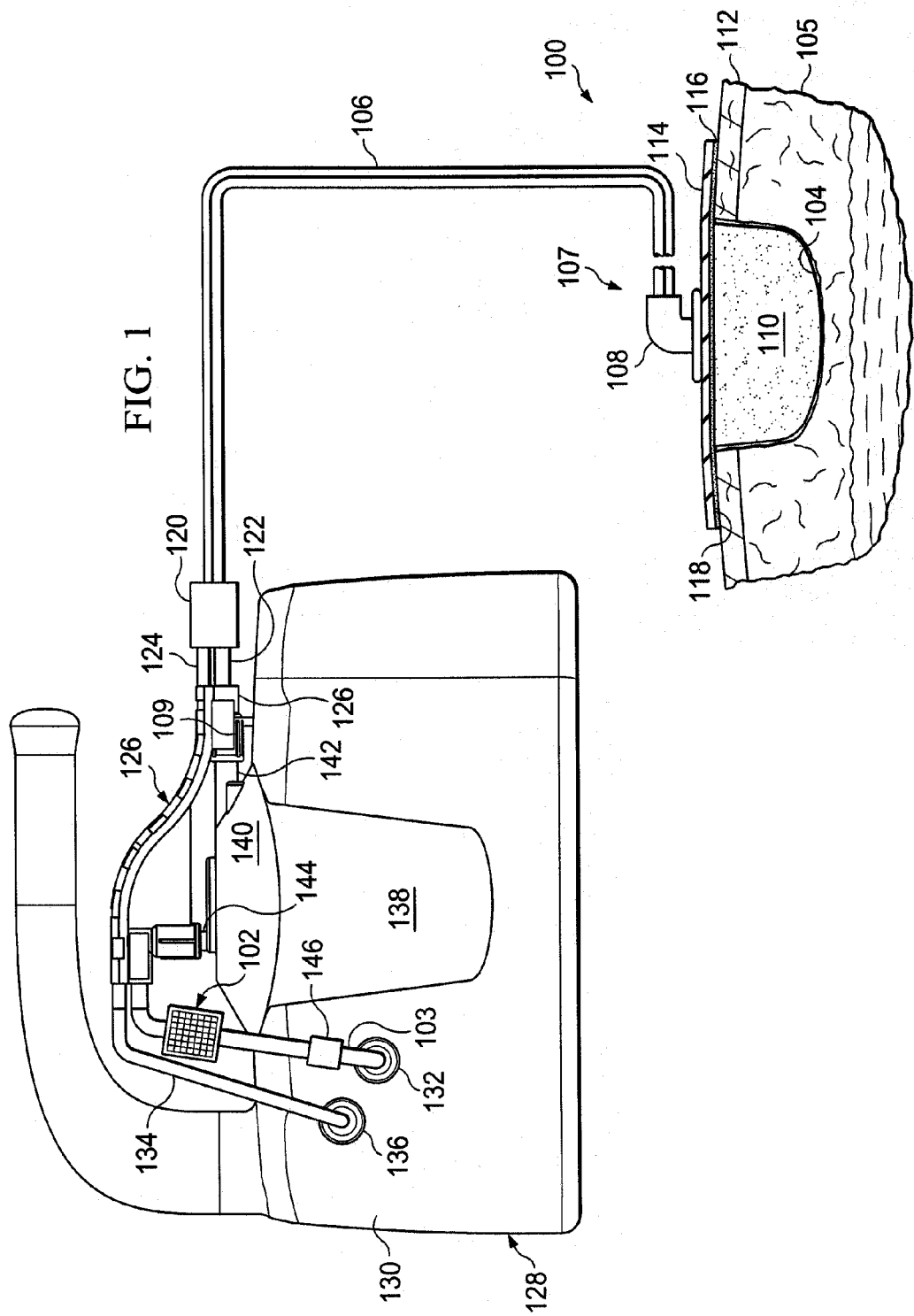
FIG. 1 is schematic diagram, with a portion shown in cross section, of a system for removing fluids from a patient with reduced pressure and including an illustrative, non-limiting embodiment of a moisture processing device.

Referring to the drawings and initially to FIG. 1, an illustrative, non-limiting embodiment of a system 100 for removing fluids from a patient is presented that includes an illustrative, non-limiting embodiment of a moisture processing device 102 on a reduced-pressure delivery conduit 103. In this illustrative embodiment, the system 100 provides reduced-pressure treatment to a tissue site 104 on a patient 105. The tissue site 104 may be the bodily tissue of any human, animal, or other organism, including bone tissue, adipose tissue, muscle tissue, dermal tissue, vascular tissue, epithelial tissue, connective tissue, cartilage, tendons, ligaments, or any other tissue. The tissue site 104 may be within a body cavity, such as an abdominal cavity. The treatment by the system 100 may include removing fluids, such as ascites or exudates, delivering of reduced pressure, or providing a protective barrier. Unless otherwise indicated, as used throughout this document, "or" does not require mutual exclusivity.

A liquid receptor 107 receives fluids from the patient 105 and delivers the fluids to a conduit 106. The liquid receptor 107 may be any device or subsystem for receiving fluids from the patient 105. For example, the liquid receptor 107 may include a suction device or reduced-pressure dressing or other means involving reduced pressure. In this instance, the liquid receptor 107 includes a reduced-pressure interface 108 that is fluidly coupled to a manifold 110 and covered by a sealing member 114. The manifold 110 is placed proximate to the tissue site 104 and receives fluids from the tissue site 104. Reduced pressure is delivered through the conduit 106 to the reduced-pressure interface 108. The reduced-pressure interface 108 delivers the reduced pressure to the manifold 110 that is adjacent the tissue site 104 and thereby may receive fluids.

The tissue site 104 is shown as a wound, or damaged area of tissue, that involves epidermis 112 and other tissue layers. A fluid seal is formed over the patient's epidermis 112 by the sealing member 114 and an attachment device 116, such as an adhesive on a patient-facing side 118 of the sealing member 114. The fluid seal involves a seal adequate to maintain reduced pressure at a desired site given the particular reduced-pressure source or subsystem involved. The conduit 106 may be a dual-lumen conduit wherein one lumen delivers reduced pressure and transports removed fluids, such as exudates or ascites. The other lumen of conduit 106 may provide a pressure-sensing lumen to allow the pressure at the tissue site 104 to be measured or otherwise determined by a remote measuring device. The conduit 106 may contain additional lumens, but in this example is a dual-lumen design. The conduit 106 may also be a single lumen.

The conduit 106 is fluidly coupled to, or in fluid communication with, an interface member 120. The interface member 120 fluidly couples the first lumen of the conduit 106 to a second reduced-pressure delivery conduit 122 and fluidly couples the second lumen of the conduit 106 to a first pressure-sensing conduit 124. The second reduced-pressure delivery conduit 122 is coupled to at least a portion of a medical canister connector, for example, first portion 109. The first pressure-sensing conduit 124 is also coupled to at least a portion of a medical canister connector, for example, second portion 126.

The first portion 109 of the medical canister connector is also coupled to the first reduced-pressure delivery conduit 103 that delivers reduced pressure from a reduced-pressure unit 128 to a canister 138. The reduced-pressure unit 128 includes a reduced-pressure source (not explicitly shown), such as a vacuum pump (not explicitly shown) or other source of reduced pressure that may be contained within a housing 130 or attached to the housing 130. The first reduced-pressure delivery conduit 103 enters the housing 130 at a reduced-pressure-housing port 132 and is fluidly coupled to the reduced-pressure source within the reduced-pressure unit 128. The first reduced-pressure delivery conduit 103 is also fluidly coupled to the first portion 109 of the medical canister connector to provide reduced pressure to the conduit 106.

The second portion 126 of the medical canister connector is coupled to a second pressure-sensing conduit 134 that delivers pressure to the reduced-pressure unit 128. The second pressure-sensing conduit 134 enters the housing 130 at a pressure-sensing-housing port 136. A measuring device (not explicitly shown) within the housing 130 of the reduced-pressure unit 128 receives the pressure from the second pressure-sensing conduit 134 and is able to measure or approximate the pressure existing at tissue site 104. It should be noted that the first pressure-sensing conduit 124 and the second pressure-sensing conduit 134 may be an integral conduit as is shown.

The canister 138, which may be held by the reduced-pressure unit 128, is fluidly coupled to the liquid receptor 107. Fluids removed from the patient 105 are delivered through the conduit 106 to the canister 138 or other fluid reservoir. The canister 138 may be any fluid reservoir for receiving and holding fluids from the patient 105. In one illustrative, non-limiting embodiment, an off-the-shelf medical canister may be used as the canister 138. The first, portion 109 and the second portion 126 of the medical canister connector may be sized and configured to work with a particular model of a medical canister. For example, in one illustrative embodiment, the canister 138 may be an 800 cc hydrophobic rigid canister, which includes a hydrophobic shutoff filter, available from Beamis Manufacturing Company of Sheboygan Falls, Wis. A lid 140 of the medical canister 138 has a patient port 142, which is horizontal (for the orientation shown in FIG. 1), and a reduced-pressure port 144, or suction port, which is vertical (for the orientation shown in FIG. 1).

A hydrophobic filter (not explicitly shown) is associated with the lid 140 and typically with the reduced-pressure port 144. Upon receiving adequate moisture, typically liquid, the first hydrophobic filter will become occluded and should prevent liquid from entering the first reduced-pressure delivery conduit 103. The first reduced-pressure delivery conduit 103 also has a hydrophobic filter 146, or pump-protection filter, to prevent liquids from reaching the reduced-pressure unit 128. The hydrophobic filter 146 may serve as backup to the hydrophobic associated with lid 140. The moisture processing device 102 may be fluidly coupled to the first reduced-pressure delivery conduit 103 between the hydrophobic filter 146 and the reduced-pressure port 144. The moisture processing device 102 removes moisture from humid air leaving the canister 138 that might otherwise condense within the first reduced-pressure delivery conduit 103 and cause the hydrophobic filter 146 to shutoff. The moisture processing device 102 may be used at other locations of the system 100.

Figure 2:
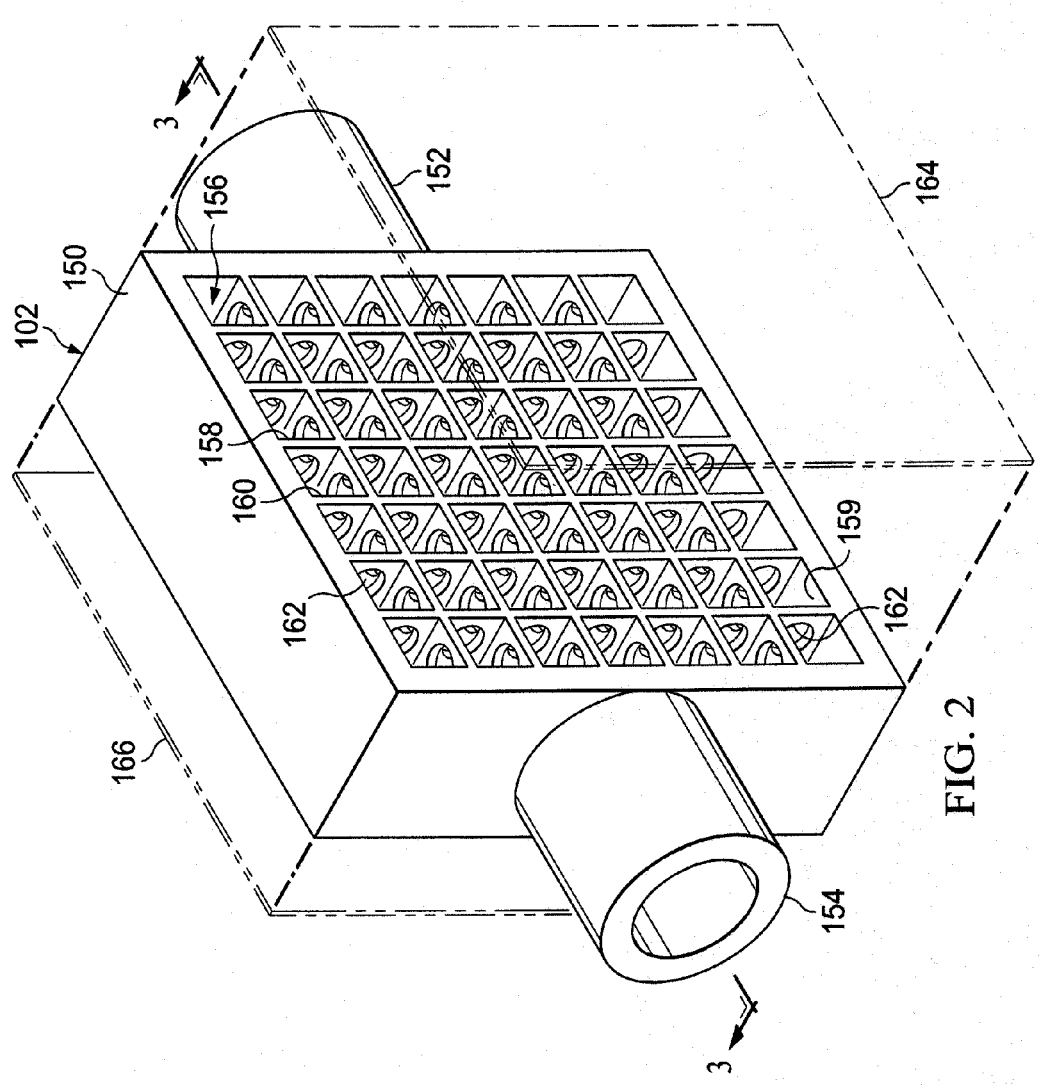
FIG. 2 is a schematic, perspective, partially-exploded view of an illustrative, non-limiting embodiment of the moisture processing device of FIG. 1.
Figure 3:
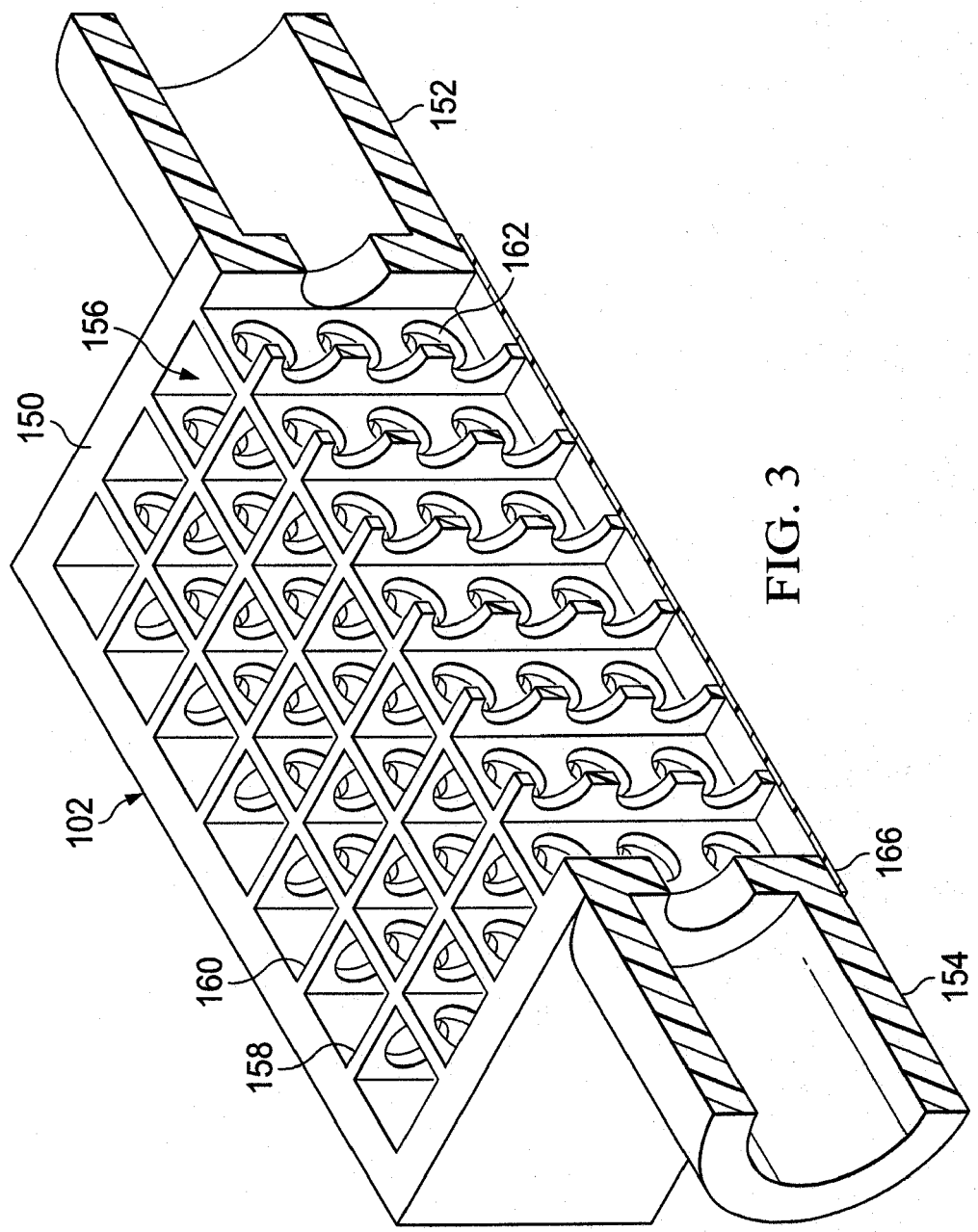
FIG. 3 is a schematic, perspective view of a portion of the moisture processing device of FIG. 2 shown with a portion in cross section taken along 3-3 in FIG. 2.

Referring now primarily to FIGS. 2 and 3, an illustrative, non-limiting embodiment of the moisture processing device 102 is presented. The moisture processing device 102 has a housing 150 formed with an inlet 152 and an outlet 154. The housing 150 forms an expanded volume 156, or chamber. With a given flow rate, Q, the fluid flow in a fluid conduit leading to inlet 152 will have a first velocity, $V_1$, associated with a first cross-sectional area, $A_1$, and upon reaching the expanded volume 156, will have a second velocity, $V_2$, for an expanded area, $A_2$. $V_1$ is greater than $V_2$ (i.e., $V_1 > V_2$). The reduction in fluid velocity ($V_1$ to $V_2$) or the increase in volume causes a reduction in temperature that in turn causes moisture in the fluid flow to condense. The resultant condensate, or condensed water, may then be processed as will be described further below.

The housing 150 may include a plurality of support members 158 that form a tortuous fluid path that may further help cause condensation to occur. For example, the plurality of support members 158 may be a grid 160 of support members having a plurality of apertures 162. The housing 150 forms a sealed space for the expanded volume 156 to retain any liquids, e.g., condensed water. The housing 150 or portions of the housing 150 may be formed from a polymer that is block molded. The housing 150 may be block-shaped to enhance the surface area made available for liquid-impermeable, vapor-permeable membranes 164, 166. The housing 150 may take other shapes as well, e.g., circular, spherical, polyhedron, oval, toroidal, or any other shape that provides an expanded volume.

At least a portion of the housing 150 is formed by the first liquid-impermeable, vapor-permeable membrane 164. The housing 150 may include one or more additional liquid-impermeable, vapor-permeable membranes, such as the second liquid-impermeable, vapor-permeable membrane 166. The liquid-impermeable, vapor-permeable membrane is a hydrophilic material such as polyurethane, cellulose and its esters, poly acrylic, poly vinyl acetate, poly vinyl alcohol, and copolymer or mixtures of these polymers. The liquid impermeable, vapor-permeable membrane is essentially non-porous so that gases such as air will not pass in through in a gross fashion, but water vapor will, i.e., the film is selective. Water vapor passes through the liquid-impermeable, vapor-permeable membrane by permeation (a product of diffusion and solvation), and although other gases will pass through under the same mechanism, water vapor passes through the liquid-impermeable, vapor-permeable membrane many times faster. Water passes through the liquid-impermeable, vapor-permeable membrane according the following: Permeability (P) equals a diffusion (D) multiplied by solubility (S). Water is more soluble in the liquid-impermeable, vapor-permeable membrane than air, for example, and will therefore move through the liquid-impermeable, vapor-permeable membrane faster than air which has a low solubility in the film. The liquid-impermeable, vapor-permeable membranes 164, 166 may be, for example, an Inspire 2301 polyurethane film without any adhesive from EXOPACK® Advance Coatings, Matthews, N.C. The liquid-impermeable, vapor-permeable membrane allows moisture and water to pass but does not allow measurable air leaks. The liquid-impermeable, vapor-permeable membrane allows vapor to egress. The egression of vapor includes condensed water that contacts the liquid-impermeable, vapor-permeable membrane and evaporates at the surface.

The liquid-impermeable, vapor-permeable membranes 164, 166 may be bonded to portions of the housing 150, e.g., a perimeter of a window opening 159, to provide a sealed space for the expanded volume 156. The plurality of support members 158 substantially supports the liquid-impermeable, vapor-permeable membrane 164 and does not allow the liquid-impermeable, vapor-permeable membrane 164 to deform to the point of damage when reduced pressure is applied to the expanded volume 156.

Referring to again to FIG. 2, an optional wicking layer (not shown) that absorbs liquids may be disposed between one or more vapor members 164, 166 and the housing 150. The wicking layer may be coextensive with the vapor member 164, 166 or may be smaller. The wicking layer may be secured with an adhesive to the housing 150, e.g., support members 158, or to an interior of the respective membrane 164, 166. The wicking layer may also be applied within the expanded volume 156. The addition of the wicking member may, in some situations, allow for greater liquid evaporation. The wicking layer in this and other embodiments may be, for example, any of the following: non-woven material, e.g., material from Libeltex; hydrophilic foams; super-absorbents, e.g., super absorbent from Luquafleece; hydrophilic sintered polymers or media; hydrophillic porous membranes (polyvinylidene fluoride (PVdF)); a sintered polymer filter material, or other materials.

Referring again primarily to FIGS. 1-2, in operation according to one illustrative embodiment, the moisture processing device 102 receives a gaseous flowing fluid from the canister 138 via the first reduced-pressure delivery conduit 103. The fluid flow enters the inlet 152 of the moisture processing device 102. As the flowing fluid enters into the expanded volume 156, moisture within the gaseous fluid flow condenses within the expanded volume 156. Further condensation may occur as the fluid flow travels through a tortuous path presented by the plurality of support members 158. The liquid, or condensate, is allowed to evaporate and the evaporated moisture may egress the housing 150 through the portions of the housing 150 that are made from the liquid-impermeable, vapor-permeable membranes, e.g., the first liquid-impermeable, vapor-permeable membrane 164. The condensate is disposed against the liquid-impermeable, vapor-permeable membrane 164 and vaporizes or otherwise egresses therethrough. A wicking layer (see, e.g., 180 in FIG. 6) may be used to attract the liquid to the first liquid-impermeable, vapor-permeable membrane 164 or other membranes. The removal of moisture from the fluid flow creates a drier fluid flow that exits the expanded volume 156 through the outlet 154.

Figure 4:
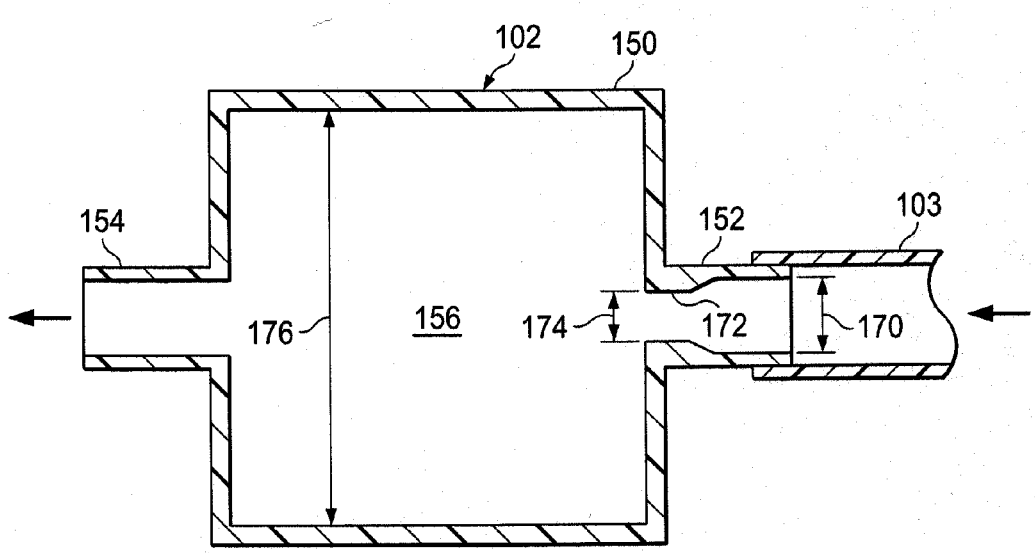
FIG. 4 is a schematic cross section of another illustrative, non-limiting embodiment of a moisture process unit.

Referring now primarily to FIG. 4, another illustrative, non-limiting embodiment of a moisture processing device 102 is presented. The moisture processing device 102 includes a housing 150 shown in cross-section that may include a plurality of support members (not shown) and one or more liquid-impermeable, vapor-permeable membranes (not shown). In this illustrative, non-limiting embodiment, a fluid flow is delivered through a first reduced-pressure delivery conduit 103 to the inlet 152 of the housing 150. The fluid flow enters an expanded volume 156 in which the temperature of the fluid decreases. The fluid flow exits the moisture processing device 102 through an outlet 154.

The inlet 152 has an entry diameter 170 ($D_1$) that transitions to a restricted area 172 having a restricted diameter 174 ($D_2$). The expanded volume 156 has a diameter or expanded diameter 176 ($D_3$). It should be appreciated that the arrangement is such that $D_3$ is greater than $D_1$ which is greater than $D_2$ (i.e., $D_3 > D_1 > D_2$). As used herein, "diameter" includes an effective diameter such that the portions identified may take any shape, but may be represented by different sized circular areas having an effective diameter. For example, a rectangular inlet having an area given by $A = L*W$ would have an effective diameter of $(L*W)/\pi$. In this embodiment, with a constant flow rate, the fluid flow entering the inlet 152 increases speed in the restricted area 172 and then decreases speed in the expanded volume 156 at the expanded diameter 176. This arrangement may further facilitate condensation within the expanded volume 156.

Figure 5:
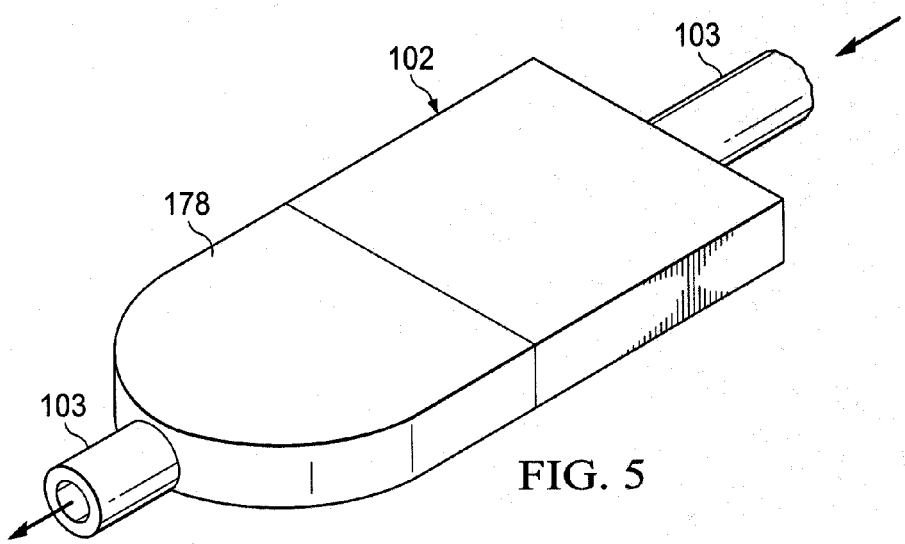
FIG. 5 is a schematic, perspective view of another illustrative, non-limiting embodiment of a moisture process unit.

Referring now primarily to FIG. 5, another illustrative, non-limiting embodiment of a moisture processing device 102 is presented. In the illustrative embodiment of FIG. 5, the moisture processing device 102, which may be like any of the embodiments or combinations of embodiments presented herein, is combined with a coupled hydrophobic filter 178. The drier fluid flow from the moisture processing device 102 is delivered directly to the hydrophobic filter 178.

In normal operation, the moisture within fluid flow being delivered by the first reduced-pressure delivery conduit 103 to the moisture processing device 102 will be substantially removed such that the hydrophobic filter 178 is not occluded in normal operation by moisture and will deliver the drier fluid flow downstream to the ongoing reduced-pressure delivery conduit 103. When the canister is full or conditions are such that a substantial amount of liquid or moisture is introduced into the fluid flow arriving at the moisture-processing device 102, the moisture-processing device becomes overloaded with moisture and the fluid flow entering the hydrophobic filter 178 contains sufficient liquid or moisture to cause the hydrophobic filter 178 to occlude. The occluded state of the hydrophobic filter 178 stops the fluid flow from flowing downstream of the hydrophobic filter 178 and thereby protects the reduced-pressure source (not shown).

Figure 6:
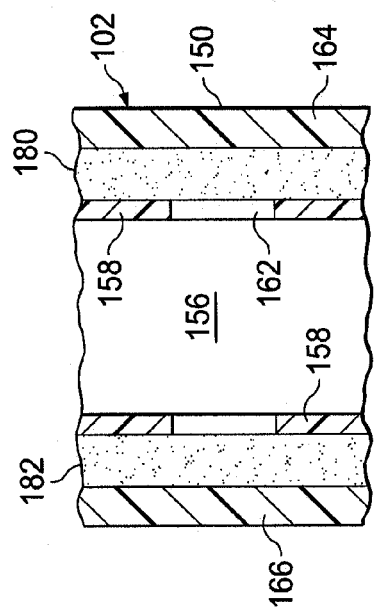
FIG. 6 is a schematic cross section of a portion of an illustrative, non-limiting embodiment of a moisture processing unit.

Referring now primarily to FIG. 6, a schematic cross-section of a portion of a housing 150 of an illustrative, non-limiting embodiment of a moisture processing device 102 is presented. In this illustrative embodiment, the cross-section shows, in simplified form, the housing 150 with a first liquid-impermeable, vapor-permeable membrane 164 having a first wicking layer 180 on an inner surface and a plurality of support members 158 in an expanded volume 156. The plurality of support members 158 may include a plurality of apertures 162. A second liquid-impermeable, vapor-permeable membrane 166 may also be included and may be adjacent to a second wicking member 182. It should be understood that more wicking members 180, 182 may be added to any of the embodiments described herein. The wicking members 180, 182 help remove any condensed liquids from the expanded volume 156 and position them substantially against the liquid-impermeable, vapor-permeable membranes 164, 166. This arrangement may further enhance evaporation and or otherwise assist with egress of the moisture.

Figure 7:
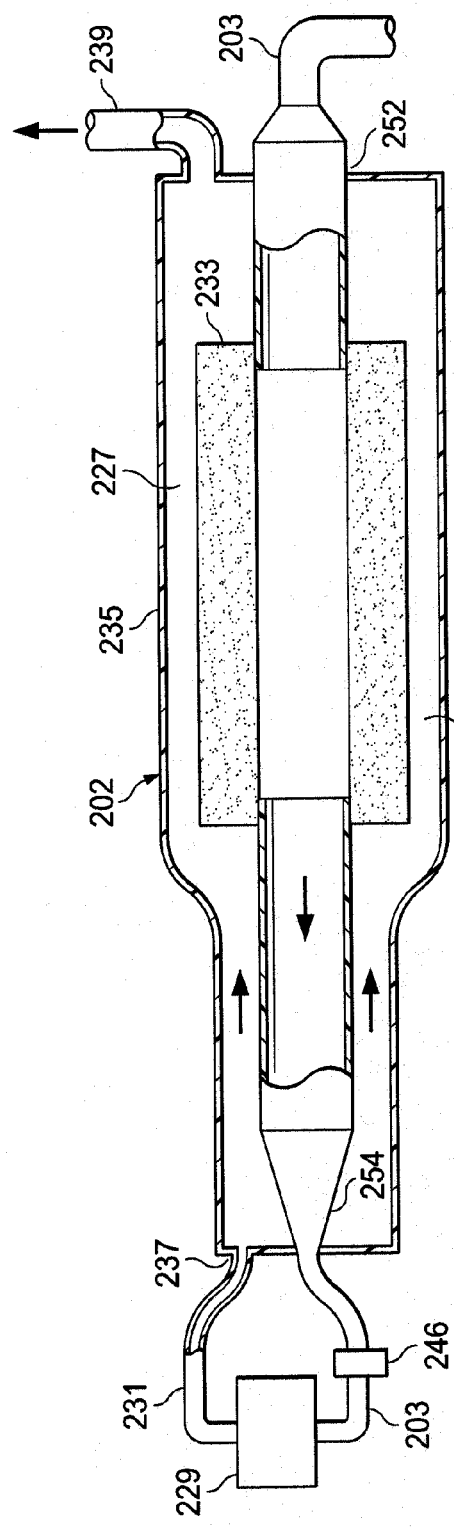
FIG. 7 is a schematic cross section of an alternative illustrative, non-limiting embodiment of a moisture process device.

Referring now primarily to FIG. 7, an alternative, illustrative, non-limiting embodiment of a portion of a system for removing fluids from a patient is presented. The liquids removed from the patient by a liquid receptor (not shown) are delivered to a canister (not shown). Reduced pressure is delivered from the reduced-pressure source 229 to the canister by a reduced-pressure delivery conduit 203. A reduced-pressure source 229, such as a micro pump or piezoelectric pump, delivers the reduced pressure to the reduced-pressure delivery conduit 203. The reduced-pressure source 229 delivers exhaust to a conduit 231. An alternative moisture processing device 202 is fluidly coupled to the reduced-pressure delivery conduit 203.

The reduced pressure in the reduced-pressure delivery conduit 203 attracts humid air or other fluids from the canister into the reduced-pressure delivery conduit 203 and at least eventually into the moisture processing device 202. The moisture processing device 202 includes a wicking material 233. The wicking material 233 may be formed from a sintered polymer filter material or other materials. The wicking material 233 forms a conduit that forms a portion of the flow path of the reduced-pressure delivery conduit 203 in the moisture processing device 202.

The fluid flow in the portion of the flow path formed by the wicking material 233 may experience a relatively substantial pressure decrease as the fluid flow moves along the wicking material 233. There may be some ingress of fluids from outside of the wicking material 233 into the reduced pressure flow path. This ingress of fluids from outside of the wicking material 233 may diminish the level of reduced pressure in the flow path and may require the reduced-pressure source 229 to produce additional reduced pressure in order to maintain a desired reduced pressure level at the tissue site or other location. Because of the pressure decrease, moisture may condense from the fluid as the fluid flows through the chamber formed by the wicking material 233. As the moisture condenses, a drier fluid flow is produced. The drier fluid leaves the wicking material 233 and continues through an outlet 254. After the outlet 254, the drier fluid enters a hydrophobic filter 246 and then arrives at the reduced-pressure source 229. The wicking material 233 is surrounded or covered, at least in part, by a cowling 235.

Exhaust from the reduced-pressure source 229 is delivered to an exhaust inlet 237 formed in the cowling 235. The exhaust continues through a diffusion path 227 between the wicking material 233 and the cowling 235. The exhaust then exits the cowling 235 through an exhaust outlet 239. Warm exhaust from the reduced-pressure source 229 moving through the diffusion path 227 may facilitate evaporation of any condensation on the wicking material 233.

While FIG. 1 shows the moisture processing device 102 as a separate unit, and FIG. 5 shows the moisture processing device 102 formed as an integral unit with the hydrophobic filter 178, other arrangements are contemplated. For example, with reference to FIG. 1, in another embodiment, the moisture processing device 102 may be incorporated into the lid 140 of the canister 138.

Systems, methods, and devices related to removing fluids from a patient are provided herein. In one instance, fluid is removed from the patient and delivered to a canister using reduced pressure. Reduced pressure is supplied to the canister via a reduced-pressure delivery conduit that includes a moisture processing device and a hydrophobic filter. The moisture processing device condenses moisture from the air to prevent condensation from occluding the hydrophobic filter. The moisture processing devices includes an expanded volume and one or more liquid-impermeable, vapor-permeable membranes. The liquid-impermeable, vapor-permeable membrane allows vapor to egress the moisture processing device. Other systems, methods, and devices are presented.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for removing fluids from a patient with reduced pressure, the system comprising:
   a liquid receptor for receiving fluids from the patient;
   a canister fluidly coupled to the liquid receptor for receiving the fluids from the patient;
   a reduced-pressure delivery conduit;
   a reduced-pressure source fluidly coupled by the reduced-pressure delivery conduit to the canister; and
   a moisture processing device fluidly coupled to the reduced-pressure delivery conduit, the moisture processing device comprising:
      a housing having an inlet and an outlet and forming an expanded volume to condense water from air entering the inlet,
      a plurality of support members in the expanded volume, and wherein the plurality of support members comprises a grid of support members having a plurality of apertures, and
      a first liquid-impermeable, vapor-permeable membrane forming at least a portion of the housing, wherein the first liquid-impermeable, vapor-permeable membrane allows vapor in the expanded volume to egress the expanded volume.

2. The system of claim 1, further comprising a first hydrophobic filter fluidly coupled to the reduced-pressure delivery conduit.

3. The system of claim 2, wherein the canister has a second hydrophobic filter associated with the canister.

4. The system of claim 1, wherein the plurality of support members form a tortuous fluid path.

5. The system of claim 1, further comprising a second liquid-impermeable, vapor-permeable membrane forming at least a portion of the housing.

6. The system of claim 2, wherein the first hydrophobic filter is coupled to the moisture processing device.

7. The system of claim 1, wherein the inlet of the moisture processing device has an entry diameter ($D_1$) transitioning to a restricted diameter ($D_2$), and then transitioning to the expanded volume, which has an expanded diameter ($D_3$), and wherein $D_3 > D_1 > D_2$.

8. The system of claim 1, further comprising a wicking layer for attracting the condensed water and holding the condensed water proximate to the first liquid-impermeable, vapor-permeable membrane.

9. A method for removing fluids from a patient with reduced pressure, the method comprising:
   removing fluids from the patient with reduced pressure;
   delivering the fluids to a canister;
   delivering reduced pressure to the canister through a reduced-pressure delivery conduit from a reduced-pressure source, whereby a fluid flow is created in the reduced-pressure delivery conduit;
   removing moisture from the fluid flow; and
   wherein the step of removing moisture comprises:
      receiving the fluid flow,
      cooling the fluid flow in a moisture processing device having a plurality of support members in an expanded volume, and wherein the plurality of support members comprises a grid of support members having a plurality of apertures to condense water from the fluid flow and to produce a drier fluid flow, and
      exposing the water to a liquid-impermeable, vapor-permeable membrane to allow evaporated water to egress the moisture processing device.

10. The method of claim 9, further comprising exposing the drier fluid flow to a first hydrophobic filter.

11. The method of claim 9, wherein the step of removing fluids from the patient with reduced pressure comprises using a manifold and a sealing member to form a sealed space over a portion of the patient.

12. The method of claim 9, wherein the moisture processing device comprises:
   a housing having an inlet and an outlet and forming the expanded volume to condense water from the fluid flow that enters the inlet, and
   a first liquid-impermeable, vapor-permeable membrane forming at least a portion of the housing, wherein the first liquid-impermeable, vapor-permeable membrane allows vapor in the expanded volume to egress the expanded volume.

13. The method of claim 9, wherein the plurality of support member form a tortuous fluid path.

14. The method of claim 12, further comprising a second liquid-impermeable, vapor-permeable membrane forming at least a portion of the housing.

15. The method of claim 12, wherein the inlet of the moisture processing device has an entry diameter ($D_1$) transitioning to a restricted diameter ($D_2$), and then transitioning to the expanded volume, which has an expanded diameter ($D_3$), and wherein $D_3 > D_1 > D_2$.

16. A method of manufacturing a system for removing fluids from a patient with reduced pressure, the method comprising:
   forming a liquid receptor;
   fluidly coupling a canister to the fluid receptor for receiving the fluids from the patient;
   providing a reduced-pressure delivery conduit;
   fluidly coupling a reduced-pressure source by the reduced-pressure delivery conduit to the canister;
   fluidly coupling a moisture processing device to the reduced-pressure delivery conduit, the moisture processing device comprising:
      a housing having an inlet and an outlet and forming an expanded volume to condense water from air entering the inlet,
      a plurality of support members in the expanded volume, wherein the plurality of support members comprises a grid of support members having a plurality of apertures, and
      a first liquid-impermeable, vapor-permeable membrane forming at least a portion of the housing, wherein the first liquid-impermeable, vapor-permeable membrane allows vapor in the expanded volume to egress the expanded volume; and
   fluidly coupling a first hydrophobic filter to the reduced-pressure delivery conduit.

17. The method of claim 16, wherein the canister has a second hydrophobic filter associated with the canister.

18. The method of claim 16, wherein the plurality of support members form a tortuous fluid path.

19. A system for removing fluids from a patient with reduced pressure, the system comprising:
- a liquid receptor for receiving fluids from the patient;
- a canister fluidly coupled to the liquid receptor for receiving the fluids from the patient;
- a reduced-pressure delivery conduit;
- a reduced-pressure source fluidly coupled by the reduced-pressure delivery conduit to the canister; and
- a moisture processing device fluidly coupled to the reduced-pressure delivery conduit, the moisture processing device comprising:
  - a housing having an inlet and an outlet and forming an expanded volume, the inlet having an entry diameter ($D_1$) transitioning to a restricted diameter ($D_2$), and the restricted diameter ($D_2$) transitioning to an expanded volume having an expanded diameter ($D_3$), the expanded diameter D3 being greater than the entry diameter D1 and the entry diameter D1 being greater than the restricted diameter D2 so that $D_3 > D_1 > D_2$, to condense water from air entering the inlet,
  - wherein all diameters are measured in the same cross sectional plane, and
  - a first liquid-impermeable, vapor-permeable membrane forming at least a portion of the housing, wherein the first liquid-impermeable, vapor-permeable membrane allows vapor in the expanded volume to egress the expanded volume.

* * * * *